US008993621B2

(12) United States Patent
Liu et al.

(10) Patent No.: US 8,993,621 B2
(45) Date of Patent: *Mar. 31, 2015

(54) CAFFEIC ACID DERIVATIVES AND THEIR USE IN IMPROVING NEURONAL CELL VIABILITY

(75) Inventors: Junyi Liu, Beijing (CN); Yansheng Du, Westfield, IN (US)

(73) Assignee: Chemigen, Inc., Indianapolis, IN (US)

( * ) Notice: Subject to any disclaimer, the term of this patent is extended or adjusted under 35 U.S.C. 154(b) by 286 days.

This patent is subject to a terminal disclaimer.

(21) Appl. No.: 13/296,305

(22) Filed: Nov. 15, 2011

(65) Prior Publication Data

US 2012/0129931 A1    May 24, 2012

Related U.S. Application Data

(60) Provisional application No. 61/413,741, filed on Nov. 15, 2010.

(51) Int. Cl.
*A01N 37/10* (2006.01)
*A61K 31/216* (2006.01)
*C07C 69/73* (2006.01)
*C07C 69/732* (2006.01)

(52) U.S. Cl.
CPC .............. *A61K 31/216* (2013.01); *C07C 69/73* (2013.01); *C07C 69/732* (2013.01)
USPC ....................................................... 514/532

(58) Field of Classification Search
None
See application file for complete search history.

(56) References Cited

U.S. PATENT DOCUMENTS

2004/0167217 A1* 8/2004 Scapagnini et al. ........... 514/543
2012/0100122 A1* 4/2012 Du .............................. 424/94.4

FOREIGN PATENT DOCUMENTS

JP   2007-230946      9/2007
WO     03/053425   *  7/2003
WO  WO-03/053425      7/2003

OTHER PUBLICATIONS

Chinthalapally et al., Cancer Research (1993), 53(18), 4182-8.*
Database CAPLUS Chemical Abstracts Service, Columbus, Ohio, US; Database Accession No. 2003:309243, Abstract of JP 2003119169, Monden et al., Apr. 23, 2003.*
Amodio et al., Int. Devl. Neuroscience 21 (2003) 379-389 (Amodio).*
"Prodrugs" in the Organic Chemistry of Drug Design and Drug Action, Silverman, Academic Press, Inc., 1992, pp. 355-357.*
Database CAPLUS Chemical Abstracts Service, Columbus, Ohio, US; Database Accession No. 1994:73208, Abstract of Kujumgiev et al., Pharmazie (1993), 48(10), 785-6.*
Mahajan et al., Indian Journal of Chemistry vol. 46B, Sep. 2007, pp. 1459-1465.*
Database CAPLUS Chemical Abstracts Service, Columbus, Ohio, US; Database Accession No. 2002:531818, Abstract of Kumazawa et al., Journal of Agricultural and Food Chemistry (2002), 50(17), 4777-4782.*
The Organic Chemistry of Drug Design and Drug Action, Silverman, Copyright © 1992 by Academic Press, Inc., pp. 355-357.*
Wei, Xing et al. Caffeic acid phenethyl ester prevents neonatal hypoxic-ischaemic brain injury, Brain, 2004, vol. 127, pp. 2629-2635.
Natarajan et al. "Caffeic acid phenethyl ester is a potent and specific inhibitor of activation of nuclear transcription factor NF-kB" Proc. Natl. Acad. Sci.; 93:9090-9095 (1996).
Fallarini, et al., "Clovamide and rosmarinic acid induce neuroprotective effects in in vitro models of neuronal death", British Journal of Pharmacology, vol. 157, No. 6, May 2009.
Kim, et al., "Total synthesis of Calebin-A, preparation of its analogues, and their neuronal cell protectivity against beta-amyloid insult" Bioorganic & Medicinal Chemistry Letters, vol. 11, No. 18, Sep. 2001.

* cited by examiner

*Primary Examiner* — Karl J Puttlitz
(74) *Attorney, Agent, or Firm* — Cesari and McKenna, LLP

(57) ABSTRACT

This invention relates to caffeic acid derivatives and improving viability of neuronal cells by contacting neuronal cells by caffeic acid derivatives as shown in the specification.

9 Claims, No Drawings

CAFFEIC ACID DERIVATIVES AND THEIR USE IN IMPROVING NEURONAL CELL VIABILITY

CROSS REFERENCE TO RELATED APPLICATIONS

This application claims priority to U.S. Provisional Application Ser. No. 61/413,741, filed Nov. 15, 2010. The contents of the prior application are hereby incorporated by reference in their entireties.

BACKGROUND

Neuronal cell death occurs in neurodegenerative disorders (including Parkinson's disease, Huntington's disease, Alzheimer's disease, multiple sclerosis, and amyotrophic lateral sclerosis), stroke, hypoxic-ischemic brain or spine injury, transplantation, and hearing loss. Compounds that improve neuronal cell viability are potential drugs for treating these conditions.

Although extensive research has been conducted in this area, there has been little success. See, e.g., Quinn, et al., Neurology, 1998, 51, S25-29. Effective drugs for treating the above-mentioned diseases are in great demand.

SUMMARY

The present invention is based on a surprising discovery that certain derivatives of caffeic acid were are effective in preventing NO-induced or glutamate-induced neuronal loss.

An aspect of this invention features derivative compounds of caffeic acid, which have formula (I) shown below:

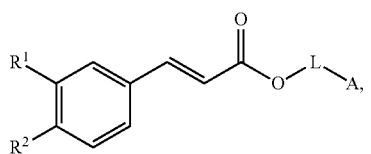

(I)

in which A is aryl, L is —CH$_2$—, and each of R$^1$ and R$^2$, independently, is —OH, —OR, or —OC(O)R, each R being C$_1$-C$_6$ alkyl; or A is aryl, L is C$_2$-C$_6$ alkylene or C$_2$-C$_6$ alkenylene, and one of R$^1$ and R$^2$ is —OC(O)R and the other is —OH, —OR, or —OC(O)R, R being C$_1$-C$_6$ alkyl.

Another aspect of this invention features a method for improving viability of neuronal cells by contacting neuronal cells with the compounds of formula (I) shown above, in which (1) A is aryl, L is C$_3$-C$_6$ alkylene or C$_2$-C$_6$ alkenylene, and each of R$^1$ and R$^2$, independently, is —OH, —OR, or —OC(O)R, R being C$_1$-C$_6$ alkyl; (2) A is aryl, L is —CH$_2$—, and each of R$^1$ and R$^2$, independently, is —OH, —OR, or —OC(O)R, R being C$_1$-C$_6$ alkyl; or (3) A is aryl, L is —CH$_2$CH$_2$—, each of R$^1$ and R$^2$, independently, is —OR or —OC(O)R, R being C$_1$-C$_6$ alkyl.

The compounds described above may further feature that L is C$_3$-C$_4$ alkylene (e.g., —CH$_2$CH$_2$CH$_2$—) or C$_2$-C$_4$ alkenylene (e.g., —CH$_2$=CH$_2$— or —CH$_2$CH=CH—), and each of R$^1$ and R$^2$ is —OH, or each of R$^1$ and R$^2$, independently, is —OR or —OC(O)R, R being methyl or ethyl.

The term "alkyl" refers to a straight, branched, or cyclic monovalent hydrocarbon containing, unless otherwise stated, 1-20 carbon atoms (e.g., C$_1$-C$_{10}$). Examples of alkyl include, but are not limited to, methyl, ethyl, n-propyl, i-propyl, n-butyl, i-butyl, t-butyl, and cyclohexyl.

The term "alkylene" refers to a straight, branched, or cyclic bivalent hydrocarbon containing, unless otherwise stated, 1-10 carbon atoms (e.g., C$_1$-C$_{10}$). Examples of alkylene include, but are not limited to, methylene (—CH$_2$—), ethylene (—CH$_2$CH$_2$—), and n-propylene (—CH$_2$CH$_2$CH$_2$—).

The term "alkenylene" refers to a straight, branched, or cyclic bivalent hydrocarbon containing one or more double bonds and, unless otherwise stated, 2-10 carbon atoms (e.g., C$_2$-C$_{10}$). Examples of alkylene include, but are not limited to, ethenylene (—CH=CH—), and n-propenylene (—CH$_2$CH=CH—).

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl.

Alkyl, alkylene, alkenylene, and aryl mentioned above include both substituted and unsubstituted moieties. Possible substituents on amino, cycloalkyl, heterocycloalkyl, cycloalkenyl, heterocycloalkenyl, aryl, and heteroaryl include, but are not limited to, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, C$_1$-C$_{10}$ alkoxy, aryl, aryloxy, heteroaryl, heteroaryloxy, amino, C$_1$-C$_{10}$ alkylamino, arylamino, hydroxy, halo, oxo (O=), thioxo (S=), thio, silyl, C$_1$-C$_{10}$ alkylthio, arylthio, C$_1$-C$_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl (—C(O)NH$_2$), carboxyl (—COOH), and carboxylic ester. On the other hand, possible substituents on alkyl, alkenyl, or alkynyl include all of the above-recited substituents except C$_1$-C$_{10}$ alkyl. Cycloalkyl, cycloalkenyl, heterocycloalkyl, heterocycloalkenyl, aryl, and heteroaryl can also be fused with each other.

The compounds described herein include the compounds themselves, as well as their salts, their solvates, and their prodrugs, if applicable. A salt, for example, can be formed between an anion and a positively charged group (e.g., amino) on a compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on an indolyl or indolinyl hydroxamate compound. Suitable cations include sodium ion, potassium ion, magnesium ion, calcium ion, and an ammonium cation such as tetramethylammonium ion. The compounds described above also include those salts containing quaternary nitrogen atoms. Examples of prodrugs include esters and other pharmaceutically acceptable derivatives, which, upon administration to a subject, are capable of providing active compounds described above.

Shown below are exemplary compounds:

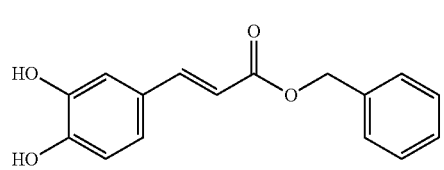

Compound 1

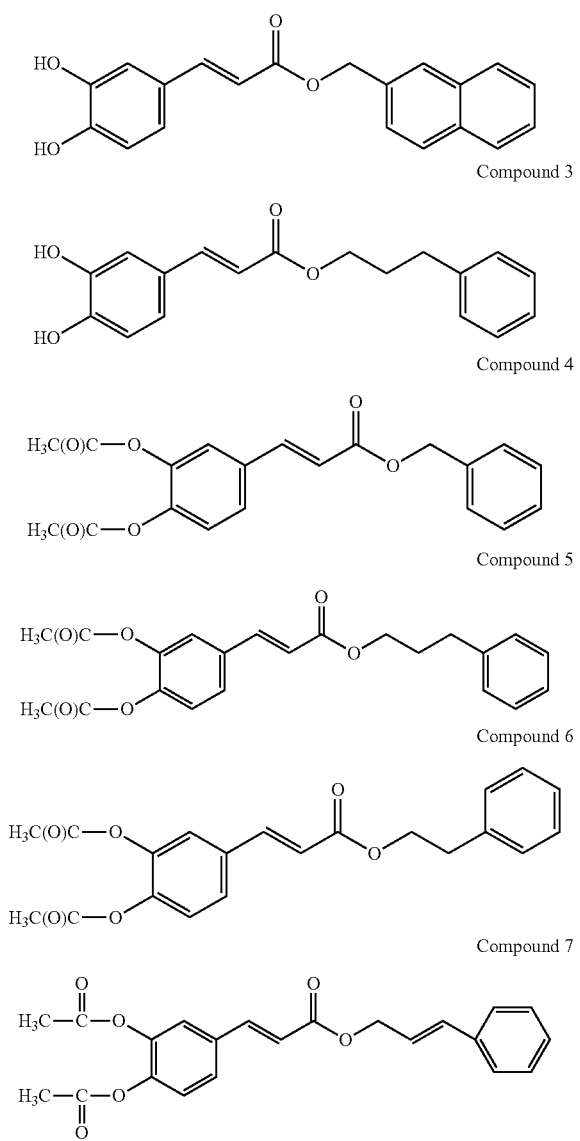

To contact a compound of formula (I) with neuronal cells in a subject in need thereof, one can administer an effective amount of this compound to the subject (e.g., a patient suffering from a neurodegenerative disorder, stroke, hypoxic-ischemic brain or spine injury, transplantation, or hearing loss) via a suitable route (e.g., intraperitoneal injection).

Thus, another aspect of this invention features a method of treating the above-mentioned diseases by one or more of the compounds of formula (I).

Also within the scope of this invention is use of a pharmaceutical composition containing one or more of these compounds for use in treating a neurodegenerative disorder, stroke, hypoxic-ischemic brain or spine injury, transplantation, or hearing loss, as well as the above-mentioned therapies and use for the manufacture of a medicament for these therapies.

The details of an embodiment of the invention are set forth in the description below. Other features, objects, and advantages of the invention will be apparent from the description and the claims.

DETAILED DESCRIPTION

The compounds of formula (I) described above can be prepared by conventional methods. For instance, they can be synthesized by chemically modifying commercially available caffeic acid to convert its COOH and/or OH groups to ester or ether groups.

Chemical transformations carried out to make the desired compounds are well known in the art. They include, but are not limited to, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Compounds thus synthesized can be further purified by flash column chromatography, high performance liquid chromatography, crystallization, or any other suitable methods.

The compounds mentioned herein contain a non-aromatic double bond. Thus, they can occur as cis- or trans-isomeric forms. All such isomeric forms are contemplated.

Also within the scope of this invention are (1) a method for improving viability of neuronal cells and (2) a method of treating neurodegenerative disorders, stroke, hypoxic-ischemic brain injury, hypoxic-ischemic spinal injury, transplantation, or hearing loss, by an effective amount of at least one of the compounds of formula (I).

Neurodegenerative disorders are characterized by progressive nervous system dysfunction. Examples include, but are not limited to, Parkinson's disease, Huntington's disease, Alzheimer's disease, multiple sclerosis, and amyotrophic lateral sclerosis.

As used herein, the term "treating" refers to administering a compound to a subject that suffers from neuronal cell loss, or has a symptom of or a predisposition toward it, with the purpose to cure, heal, alleviate, relieve, alter, remedy, ameliorate, improve, affect, or reduce the risk of neuronal cell loss, the symptoms of or the predisposition toward it. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

To practice the method of this invention, one of the above-described compounds can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. To facilitate the administration, the compound may be processed to form various suitable pharmaceutical compositions.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A composition containing one of the compounds of this invention can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. One or more solubilizing agents (e.g., cyclodextrins) which form more soluble complexes with the compounds of this invention can be utilized as pharmaceutical carriers for delivery of the active compounds. Examples of other carriers include colloidal silicon dioxide, magnesium stearate, sodium lauryl sulfate, and D&C Yellow #10.

Suitable in vitro assays can be used to preliminarily evaluate the efficacy of the compounds described above in preventing neuronal cell loss. See the actual examples provided below. The effective compounds can further be examined for their efficacy in treating various diseases either in vivo. For example, a compound can be administered to an animal (e.g., a mouse model) having neurodegenerative disorders, stroke, hypoxic-ischemic brain or spine injury, transplantation, or hearing loss and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Chemical Syntheses
Synthesis of Compounds 1-3

300 mg (1.66 mmol) of caffeic acid was dissolved in 3.15 ml DMSO. $K_3PO_4$ (2.00 mmol) was added while stirring. Stirring was continued for 30 minutes. At the end, a solution of 1.70 mmol of benzyl bromide in 1.05 ml DMSO was added slowly within 30 minutes. The resulting reaction mixture was stirred at room temperature for 9 hrs and then at 15° C. for 12 hrs. The reaction mixture was slowly added to 20 ml of ice water and extracted with ethyl acetate (3×10 ml). The aqueous layer was acidified by dropwise addition of 1.0 M aqueous HCl and extracted with ethyl acetate. The combined organic layers were washed sequentially with 1.0 M HCl (2.5 ml) and saturated sodium chloride solution (3×10 ml), dried over anhydrous $Na_2SO_4$, filtered, and concentrated under reduced pressure. The crude material was purified by silica gel chromatography using petroleum ether/ethyl acetate gradient eluent (from 20:1 to 3:1 V/V) and Compound 1 was obtained at a yield of more than 80%.

Compounds 2 and 3 were prepared in the same manner except that naphthylmethyl bromide and bromopropylbenzene were respectively used, instead of benzyl bromide.

Compound 1: $^1$H NMR (300 MHz, DMSO-$D_6$) δ: 9.63 (s, 1H, OH), 9.16 (s, 1H, OH), 7.53 (d, J=15.6 Hz, 1H, C3-H), 6.75~7.43 (m, 8H, Ar—H), 6.33 (d, J=15.9 Hz, 1H, C2-H), 5.20 (s, 2H, $CH_2$); MS (ESI$^+$): [M+H]$^+$ m/z 271, [M+Na]$^+$ m/z 293; m.p.: 150-151° C.

Compound 2: $^1$H NMR (300 MHz, DMSO-$d_6$) δ: 9.371 (brs, 2H, 2×OH), 7.91~9.94 (m, 4H, Ar—H), 7.55 (d, J=15.9 Hz, 1H, C3-H), 7.50~7.54 (m, 3H, Ar—H), 7.00~7.07 (m, 2H, Ar—H), 6.76 (d, J=8.1 Hz, 1H, Ar—H), 6.36 (d, J=15.9 Hz, 1H, C2-H), 5.35 (s, 2H, $CH_2$); $^{13}$C NMR (75 MHz, DMSO-$d_6$) δ: 166.5, 148.5, 145.7, 145.6, 134.1, 132.8, 132.6, 128.2, 127.9, 127.6, 126.8, 126.4, 126.3, 125.9, 125.5, 121.6, 115.7, 114.9, 113.7, 65.4; MS (ESI$^-$): [M–H]$^-$ m/z 319; m.p.: 172-175° C.

Compound 3: $^1$H NMR 300 MHz, DMSO-$d_6$) δ: 9.21 (brs, 2H, OH), 7.46 (d, J=15.9 Hz, 1H, C3-H), 6.75~7.34 (m, 8H, Ar—H), 6.24 (d, J=15.9 Hz, 1H, C2-H), 4.32 (t, J=6.9 Hz, 2H, COO$\underline{CH_2}CH_2$), 2.95 (t, J=6.9 Hz, 2H, COOCH$_2\underline{CH_2}$); MS (FAB): [M+H]$^+$ m/z 285; m.p.: 102~103° C.

Synthesis of Compounds 4-7

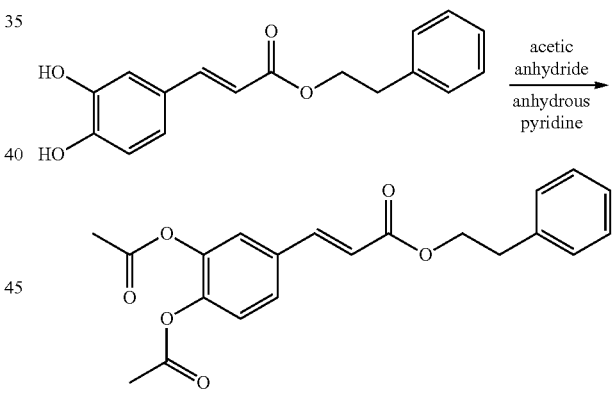

2.5 mmol of caffeic acid phenethyl ester was dissolved in 6 ml acetic anhydride. To this was added 5 mmol (0.43 ml) anhydrous pyridine while stirring. After stirred at room temperature for 5 minutes, the reaction mixture was then slowly added to 30 ml of ice water while stirring and then extracted with ethyl acetate (3×10 ml). The combined organic layers were washed with saturated sodium chloride solution (3×10 ml). The organic layer was dried over anhydrous MgSO$_4$, filtered, and concentrated under reduced pressure. The crude material was purified by silica gel chromatography using of petroleum ether/ethyl acetate gradient eluent (from 20:1 to 8:1 V/V) to give Compound 6 at a yield of 96%.

Compounds 4-7 were prepared by in the same manner except that different starting maters were used.

Compound 4: $^1$H NMR (300 MHz, CDCl$_3$) δ: 7.66 (d, J=15.9 Hz, 1H, C3-H), 7.20~7.40 (m, 8H, Ar—H), 6.43 (d, J=15.9 Hz, C2-H), 5.24 (s, 2H, CH$_2$), 2.29 (s, 6H, 2×CH$_3$);

$^{13}$C NMR (75 MHz, CDCl$_3$) δ: 168.0, 167.9, 166.3, 143.5, 143.1, 142.3, 135.8, 133.1, 128.5, 128.2, 126.3, 123.9, 122.7, 119.0, 66.4, 20.6, 20.5; MS ($^+$ESI-TOF): [M+NH$_4$]$^+$ m/z 372, [M+Na]$^+$ m/z 377; m.p.: 101~103° C.

Compound 5: $^1$H NMR (300 MHz, CDCl$_3$) δ: 7.60 (d, J=16.2 Hz, 1H, C3-H), 7.20~7.43 (m, 8H, Ar—H), 6.39 (d, J=15.9 Hz, 1H, C2-H), 4.22 (t, J=6.6 Hz, 2H, phCH$_2$CH$_2$CH$_2$), 2.74 (t, J=7.5 Hz, 2H, phCH$_2$CH$_2$CH$_2$), 2.31 (s, 3H, CH$_3$), 2.30 (s, 3H, CH$_3$), 2.04 (m, 2H, phCH$_2$CH$_2$CH$_2$); $^{13}$C NMR (75 MHz, CDCl$_3$) δ: 168.0, 167.9, 166.5, 143.4, 142.7, 142.4, 141.1, 133.2, 128.5, 126.3, 126.0, 123.9, 123.8, 122.7, 122.6, 119.3, 63.9, 32.2, 30.2, 20.7, 20.5; MS (ESI$^+$): [M+H]$^+$ m/z 383, [M+NH$_4$]$^+$ m/z 400; m.p.: 65~67° C.

Compound 6: $^1$H NMR (300 MHz, CDCl$_3$) δ: 7.60 (d, J=15.9 Hz, 1H, C3-H), 7.20~7.57 (m, 8H, Ar—H), 6.36 (d, J=15.9 Hz, 1H, C2-H), 4.41 (t, J=7.2 Hz, 2H, COOCH$_2$CH$_2$), 3.01 (t, J=7.2 Hz, 2H, COOCH$_2$CH$_2$), 2.30 (6H, 2×CH$_3$); $^{13}$C NMR (75 MHz, CDCl$_3$) δ: 168.0, 167.9, 166.4, 143.4, 142.8, 142.4, 137.7, 133.2, 128.9, 128.5, 126.5, 126.4, 123.9, 122.7, 119.2, 65.1, 35.1, 20.6; MS ($^+$ESI-TOF): [M+NH$_4$]$^+$ m/z 369, [M+NH$_4$]$^+$ m/z 386, [M+Na]$^+$ m/z 391, [M+K]$^+$ m/z 407; m.p.: 82-83° C.

Compound 7: $^1$H NMR (300 MHz, CDCl$_3$) δ: 7.66 (d, J=16.2 Hz, 1H, C3-H), 7.21~7.43 (8H, Ar—H), 6.71 (d, J=15.9 Hz, 1H, CH$_2$CH=CH), 6.42 (d, J=15.9 Hz, 1H, C2-H), 6.30~6.38 (m, 1H, CH$_2$CH=CH), 4.87 (d, J=7.5 Hz, 2H, CH$_2$), 2.30 (s, 6H, 2×CH$_3$); $^{13}$C NMR (75 MHz, CDCl$_3$) δ: 168.0, 167.9, 166.3, 143.5, 143.1, 142.4, 136.1, 134.3, 133.2, 128.6, 128.0, 126.6, 123.9, 123.8, 123.0, 122.8, 122.6, 119.0, 65.2, 20.6, 20.5); MS ($^+$ESI-TOF): [M+NH$_4$]$^+$ m/z 398, [M+Na]$^+$ m/z 403; m.p.: 86~88° C.

Biological Assay

Efficacy of caffeic acid derivatives on improving neuronal cell viability was assessed according to a method described in Du et al., Proc. Natl. Acad. Sci., 1997, 94: 11657-11662; and Du et al., Proc. Natl. Acad. Sci., 2001, 98:14669-14674.

Briefly, freshly dissected cerebella were disrupted and the cerebellar granule neuron (CGN) cells were seeded at a density of 1.2 to 1.5×10$^6$ cells/ml on poly-L-lysine coated plates in a basal medium Eagle supplemented with 10% fetal bovine serum (FBS), 25 mM KCL, and gentamicin (0.1 mg/ml). Cytosine arabinoside (10 µM) was added to the culture medium 24 h after initial plating. In all experiments, CGNs were utilized after 7-8 days in vitro. CGNs treated with Glutamate (30 µM) or sodium nitroprusside (SNP, 50 µM) for 24 hours were used as control. CGNs were first treated with Compounds 1-7 in DMSO (10 µM) for 2 hours and then treated with Glutamate (30 µM) or SNP (50 µM) for 24 hours. Neuronal viability was assessed by MTT assay as follows: MTT (3-(4,5-Dimethylthiazol-2-yl)-2,5-diphenyltetrazolium bromide, 500 µM) was added and cultured for after 15 minutes at 37° C. After the cultures were washed with saline, DMSO was added in the dark since MTT to dissolve purple formazan dye crystals. After 15 minutes at 37° C., absorbance was measured by a plate reader at 570 nm with a reference wavelength of 650 nm.

The results show that treatment of CGNs with Glutamate and SNP resulted in neuronal death, but pretreatment of CGNs with each of Compounds 1-7 significantly prevented the Glutamate and SPN-induced neuronal dealth.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for improving viability of neuronal cells, the method comprising contacting neuronal cells with an effective amount of a compound of formula (I):

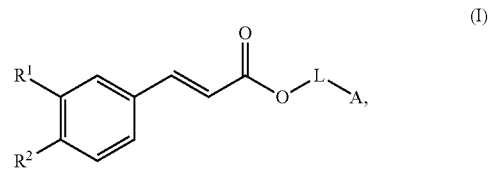

wherein
A is aryl;
L is $C_3$-$C_6$ alkylene, or $C_2$-$C_6$ alkenylene; and
each of R$^1$ and R$^2$, independently, is —OR, or —OC(O)R, R being $C_1$-$C_6$ alkyl, wherein the compound is capable of inhibiting glutamate or sodium nitroprusside-induced neuronal loss.

2. The method of claim 1, wherein L is —CH$_2$CH$_2$CH$_2$— or —CH$_2$—CH=CH—, and each of R$^1$ and R$^2$, independently, is —OR or —OC(O)R, R being methyl or ethyl.

3. The method of claim 1, wherein the compound is

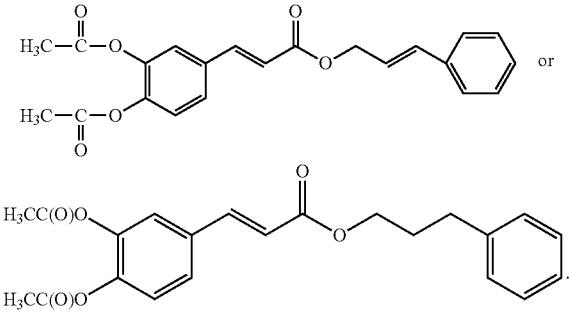

4. The method of claim 1, wherein the contacting step is performed by administering the compound to a patient such that it reaches neuronal cells in the patient and improves their viability.

5. The method of claim 4, wherein the patient suffers from a neurodegenerative disorder, stroke, hypoxic-ischemic brain injury, or hypoxic-ischemic spinal injury.

6. A method for improving viability of neuronal cells, the method comprising contacting neuronal cells with an effective amount of a compound of formula (I):

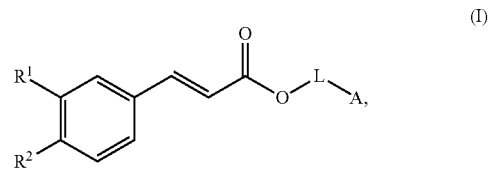

wherein
A is aryl;
L is —CH$_2$—; and
each of R$^1$ and R$^2$, independently, is —OR, or —OC(O)R, R being $C_1$-$C_6$ alkyl, wherein the compound is capable of inhibiting glutamate or sodium nitroprusside-induced neuronal loss.

7. The method of claim 6, wherein the compound is

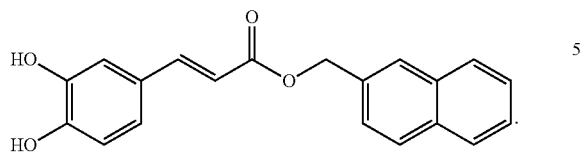

8. The method of claim 6, wherein the contacting step is performed by administering the compound to a patient such that it reaches neuronal cells in the patient and improves their viability.

9. The method of claim 8, wherein the patient suffers from a neurodegenerative disorder, stroke, hypoxic-ischemic brain injury, or hypoxic-ischemic spinal injury.

* * * * *